(12) United States Patent
Naidu (10) Patent No.: US 12,042,611 B2
(45) Date of Patent: Jul. 23, 2024

(54) NEEDLE SHIELD

(71) Applicant: Becton, Dickinson and Company, Franklin Lakes, NJ (US)

(72) Inventor: Jithendra Kumar Sathyanarayana Naidu, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 265 days.

(21) Appl. No.: 17/192,778

(22) Filed: Mar. 4, 2021

(65) Prior Publication Data

US 2021/0290912 A1     Sep. 23, 2021

Related U.S. Application Data (60) Provisional application No. 62/993,390, filed on Mar. 23, 2020.

(51) Int. Cl.
| | | |
|---|---|---|
| *A61M 25/06* | (2006.01) | |
| *A61M 25/00* | (2006.01) | |
| *A61M 39/10* | (2006.01) | |
| *A61M 5/32* | (2006.01) | |
| *A61M 39/04* | (2006.01) | |

(52) U.S. Cl.
CPC .... *A61M 25/0618* (2013.01); *A61M 25/0097* (2013.01); *A61M 25/0606* (2013.01); *A61M 25/0631* (2013.01); *A61M 39/10* (2013.01); *A61M 5/321* (2013.01); *A61M 2005/3247* (2013.01); *A61M 2005/325* (2013.01);
(Continued)

(58) Field of Classification Search
CPC .......... A61M 25/0618; A61M 25/0631; A61M 25/0606; A61M 39/10; A61M 2039/1077; A61M 2039/1072; A61M 25/0097; A61M 2005/325; A61M 2005/3247; A61M 5/158; A61M 5/321; A61M 2039/042
See application file for complete search history.

(56) References Cited

U.S. PATENT DOCUMENTS

2008/0249478 A1 * 10/2008 Ishikura ............ A61M 25/0618
604/198
2012/0277679 A1   11/2012 Steube
(Continued)

FOREIGN PATENT DOCUMENTS

| CN | 107050622 A | 8/2017 |
|---|---|---|
| EP | 2517751 | 10/2012 |

(Continued)

*Primary Examiner* — William R Carpenter
*Assistant Examiner* — Robert F Allen
(74) *Attorney, Agent, or Firm* — Kirton McConkie; Whitney Blair; Kevin Stinger (57) ABSTRACT

A shield for a needle of a peripheral intravenous catheter or other IV catheter system is provided. The shield may be formed of a single piece of material that may be bent to form a top portion, a bottom portion, a proximal portion, a top distal portion and a bottom distal portion. The proximal portion may form a proximal needle opening and the top or bottom distal portion may form a distal needle opening to allow a needle to extend through the shield when the shield is positioned within the lumen of a catheter adapter. When the distal tip of the needle is withdrawn proximally, the shield may transition from an unlocked position to a locked position in which the distal tip will be retained within the shield.

17 Claims, 7 Drawing Sheets

(52) U.S. Cl.
CPC .......... *A61M 2039/042* (2013.01); *A61M 2039/1072* (2013.01); *A61M 2039/1077* (2013.01)

(56) References Cited

U.S. PATENT DOCUMENTS

| | | |
|---|---|---|
| 2013/0079720 A1 | 3/2013 | Finnestad et al. |
| 2014/0018738 A1 | 1/2014 | Steube |
| 2014/0100528 A1 | 4/2014 | Finnestad et al. |
| 2017/0151419 A1 | 6/2017 | Sonksen |
| 2018/0214682 A1* | 8/2018 | Woehr .............. A61M 39/0613 |
| 2018/0289932 A1* | 10/2018 | Isaacson ........... A61M 25/0618 |
| 2019/0134356 A1 | 5/2019 | Hulvershorn et al. |

FOREIGN PATENT DOCUMENTS

| | | |
|---|---|---|
| EP | 2760520 A1 | 6/2014 |
| EP | 3175881 A1 | 6/2017 |
| ES | 2662356 T3 | 4/2018 |
| JP | 2017099884 A | 6/2017 |
| WO | 2013048975 A1 | 4/2013 |
| WO | 2017214110 A1 | 12/2017 |

* cited by examiner

NEEDLE SHIELD

RELATED APPLICATIONS

This application claims the benefit of U.S. Provisional Patent Application No. 62/993,390, filed on Mar. 23, 2020, entitled "NEEDLE SHIELD," which is incorporated herein in its entirety.

BACKGROUND

Intravenous (IV) catheter systems are commonly used for a variety of infusion therapies. For example, an IV catheter system may be used for infusing fluids, such as normal saline solution, various medicaments, and total parenteral nutrition, into a patient. IV catheter systems may also be used for withdrawing blood from the patient.

A common type of IV catheter system is an over-the-needle peripheral intravenous ("IV") catheter ("PIVC"). As its name implies, the over-the-needle catheter may be mounted over a needle having a sharp distal tip. The catheter and the needle may be assembled so that the distal tip of the needle extends beyond the distal tip of the catheter with the bevel of the needle facing up away from skin of the patient. The catheter and needle are generally inserted at a shallow angle through the skin into the vasculature of the patient.

After the catheter has been inserted into the patient's vasculature, the needle is withdrawn from the catheter and the catheter adapter. To prevent contact with the sharp distal tip of the needle, the needle assembly may oftentimes include a shield that isolates the distal tip once the introducer is withdrawn from the catheter adapter.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a shield for a needle of a peripheral intravenous catheter (PIVC) or other IV catheter system. The shield may be formed of a single piece of material that may be bent to form a top portion, a bottom portion, a proximal portion, a top distal portion and a bottom distal portion. The proximal portion may form a proximal needle opening and the top or bottom distal portion may form a distal needle opening to allow a needle to extend through the shield when the shield is positioned within the lumen of a catheter adapter. When the distal tip of the needle is withdrawn proximally, the shield may transition from an unlocked position to a locked position in which the distal tip will be retained within the shield.

In some embodiments, a shield for a needle may include a top portion forming a top surface and opposing side surfaces that extend downwardly from the top surface. In some embodiments, the shield may include a bottom portion forming a bottom surface and opposing side surfaces that extend upwardly from the bottom surface. In some embodiments, the shield may include a proximal portion that interconnects the top portion and the bottom portion. In some embodiments, the proximal portion may form a proximal needle opening. In some embodiments, the shield may include a top distal portion that extends downwardly from the top surface. In some embodiments, the shield may include a bottom distal portion that extends upwardly from the bottom surface. In some embodiments, when the shield is in an unlocked position, the top distal portion and the bottom distal portion may be spaced to expose a distal needle opening. In some embodiments, when the shield is in a locked position, the top distal portion and the bottom distal portion may not expose the distal needle opening.

In some embodiments, the top distal portion may include one or more tabs and the bottom distal portion may include one or more notches for receiving the one or more tabs to maintain the shield in the locked position. In some embodiments, the distal needle opening may be formed in the top distal portion. In some embodiments, two tabs may be positioned on opposing sides of the top distal portion and the distal needle opening may be formed between the two tabs. In some embodiments, two notches may be positioned on opposing sides of the bottom distal portion.

In some embodiments, when the shield is in the unlocked position, the top distal portion and the bottom distal portion may not overlap, whereas, when the shield is in the locked position, the top distal portion and the bottom distal portion may overlap. In some embodiments, when the shield is in the unlocked position, the opposing side surfaces of the top portion may partially overlap the opposing side surfaces of the bottom portion, whereas, when the shield is in the locked position, the opposing side surfaces of the top portion may fully overlap the opposing side surfaces of the bottom portion.

In some embodiments, the top surface and the bottom surface may each form a protrusion for retaining the shield within a catheter adapter while a needle passes through the proximal needle opening and the distal needle opening. In some embodiments, the top portion, the bottom portion, the proximal portion, the top distal portion and the bottom distal portion may all be formed from a single piece of material. In some embodiments, the single piece of material may be sheet metal.

In some embodiments, an intravenous catheter system may include a catheter assembly having a catheter adapter forming a lumen and a catheter that extends distally from the catheter adapter. In some embodiments, the intravenous catheter system may include a needle assembly having a needle hub and a needle that extends distally from the needle hub. In some embodiments, the needle assembly may be configured to couple to the catheter assembly to cause the needle to extend through the lumen of the catheter adapter and the catheter. In some embodiments, the intravenous catheter system may include a shield positioned within the lumen of the catheter adapter. In some embodiments, the shield may include a top portion forming a top surface and opposing side surfaces that extend downwardly from the top surface. In some embodiments, the shield may include a bottom portion forming a bottom surface and opposing side surfaces that extend upwardly from the bottom surface. In some embodiments, the shield may include a proximal portion that interconnects the top portion and the bottom portion. In some embodiments, the proximal portion may form a proximal needle opening. In some embodiments, the shield may include a top distal portion that extends downwardly from the top surface. In some embodiments, the shield may include a bottom distal portion that extends upwardly from the bottom surface. In some embodiments, when the needle assembly is coupled to the catheter adapter, the needle may extend through the proximal needle opening and a distal needle opening of the shield to thereby maintain the shield in an unlocked position, whereas, when the needle assembly is withdrawn proximally from the catheter assembly to cause a distal tip of the needle to pass through the distal needle opening, the shield may transition to a locked position in which the distal tip of the needle is prevented from passing distally through the distal needle opening.

In some embodiments, the top surface and the bottom surface of the shield may each form a protrusion. In some embodiments, the catheter adapter may include slots that may receive the protrusions formed in the top and bottom surfaces when the shield is in the unlocked position. In some embodiments, the top distal portion may include one or more tabs and the bottom distal portion may include one or more notches for receiving the one or more tabs to maintain the shield in the locked position. In some embodiments, the distal needle opening may be formed in the top distal portion. In some embodiments, two tabs may be positioned on opposing sides of the top distal portion and two notches may be positioned on opposing sides of the bottom distal portion. In some embodiments, the catheter assembly may include a septum positioned in the lumen of the catheter adapter distal to the shield. In some embodiments, the needle may extend through the septum when the needle assembly is coupled to the catheter assembly. In some embodiments, the top portion, the bottom portion, the proximal portion, the top distal portion and the bottom distal portion may all be formed from a single piece of material.

In some embodiments, a peripheral intravenous catheter may include a catheter assembly having a catheter adapter forming a lumen and a catheter that extends distally from the catheter adapter. In some embodiments, the peripheral intravenous catheter may include a needle assembly having a needle hub and a needle that extends distally from the needle hub. In some embodiments, the needle assembly may be configured to couple to the catheter assembly to cause the needle to extend through the lumen of the catheter adapter and the catheter. In some embodiments, the peripheral intravenous catheter may include a shield positioned within the lumen of the catheter adapter. In some embodiments, the shield may be formed of a single piece of material. In some embodiments, the shield may include a top portion forming a top surface and opposing side surfaces that extend downwardly from the top surface. In some embodiments, the shield may include a bottom portion forming a bottom surface and opposing side surfaces that extend upwardly from the bottom surface. In some embodiments, the shield may include a proximal portion that interconnects the top portion and the bottom portion. In some embodiments, the proximal portion may form a proximal needle opening. In some embodiments, the shield may include a top distal portion that extends downwardly from the top surface. In some embodiments, the shield may include a bottom distal portion that extends upwardly from the bottom surface. In some embodiments, when the needle assembly is coupled to the catheter adapter, the needle may extend through the proximal needle opening and a distal needle opening of the shield to thereby maintain the shield in an unlocked position, whereas, when the needle assembly is withdrawn proximally from the catheter assembly to cause a distal tip of the needle to pass through the distal needle opening, the shield may transition to a locked position in which the distal tip of the needle is prevented from passing distally through the distal needle opening.

In some embodiments, the top surface and the bottom surface of the shield may each form a protrusion. In some embodiments, the catheter adapter may include slots that receive the protrusions formed in the top and bottom surfaces when the shield is in the unlocked position. In some embodiments, the top distal portion may include one or more tabs and the bottom distal portion may include one or more notches for receiving the one or more tabs to maintain the shield in the locked position.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
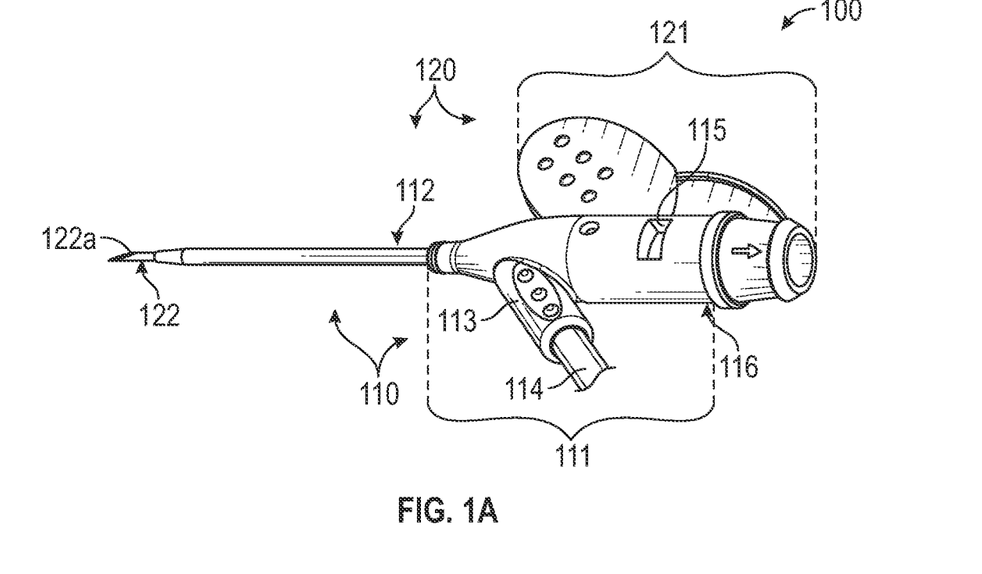
FIG. 1A illustrates a PIVC that is configured in accordance with some embodiments.

FIG. 1A provides an example of a PIVC 100 that is configured in accordance with some embodiments of the present disclosure. PIVC 100 may include a catheter assembly 110 and a needle assembly 120. Catheter assembly 110 may include a catheter adapter 111 from which a catheter 112 may extend distally. Needle assembly 120 may include a needle hub 121 from which a needle 122 may extend distally. Needle assembly 120 may be inserted into a proximal end 116 of catheter adapter 111 to couple needle assembly 120 to catheter assembly 110, which in turn may cause distal tip 122a of needle 122 to extend distally from catheter 112. Catheter adapter 111 may include a pair of slots 115 positioned on opposite sides of the catheter adapter. In some embodiments, catheter adapter 111 may include an extension port 113 by which an extension set 114 may be integrated into PIVC 100.

Figure 1B:
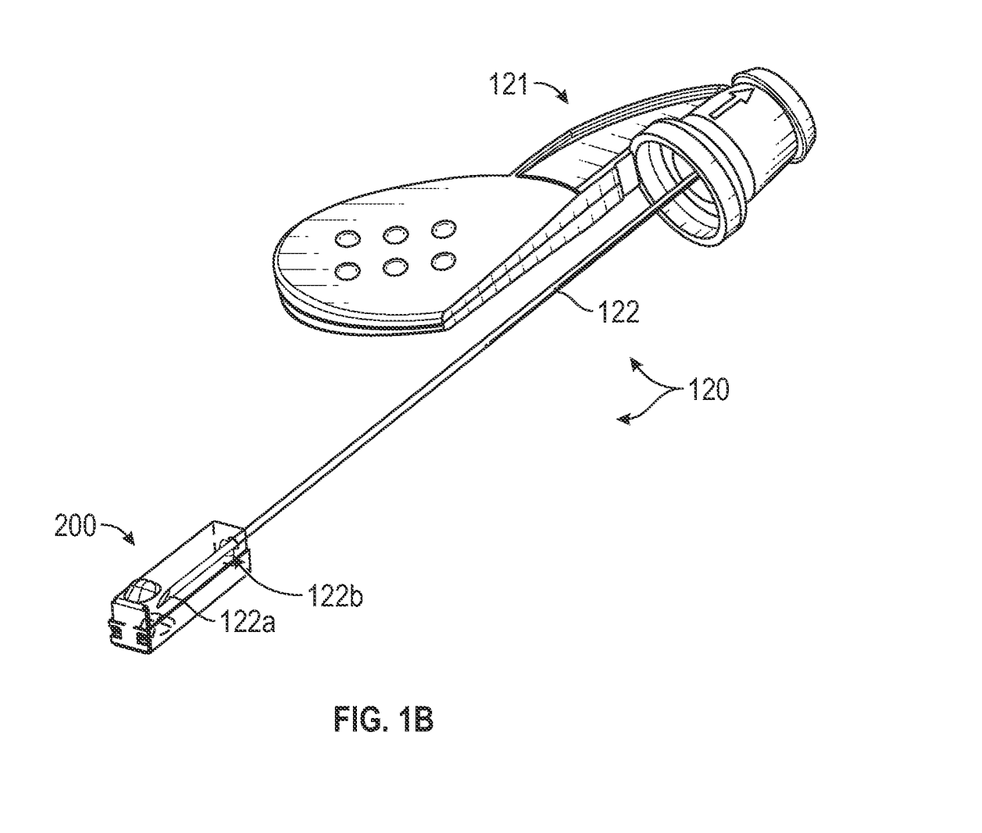
FIG. 1B illustrates a needle assembly of the PIVC of FIG. 1A when removed from the catheter assembly including how a shield configured in accordance with some embodiments secures the distal tip of the needle.

FIG. 1B illustrates needle assembly 120 after it has been withdrawn and separated from catheter adapter 111. In accordance with some embodiments, a shield 200 may be employed within PIVC 100 to secure distal tip 122a of needle 122 as needle assembly 120 is withdrawn. In some embodiments, needle 122 may include a section of expanded cross-sectional area or "bump" 122b that may prevent needle 122 from being separated from shield 200 as is further described below.

Figure 2A:
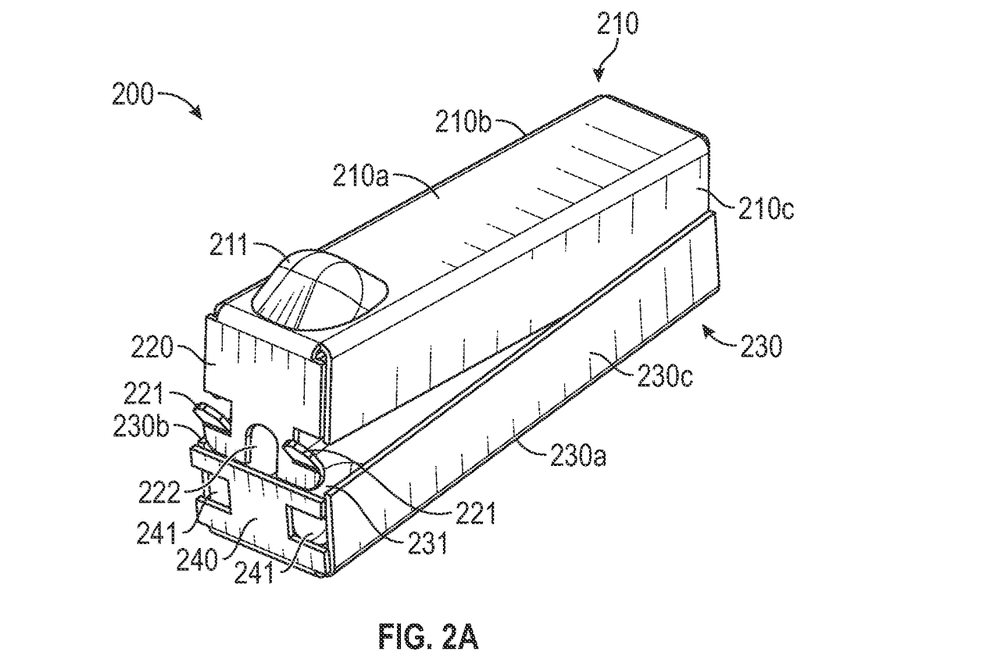
FIGS. 2A-2C are top perspective, distal and side views respectively of a shield that is configured in accordance with some embodiments when the shield is in an unlocked position.
Figure 2B:
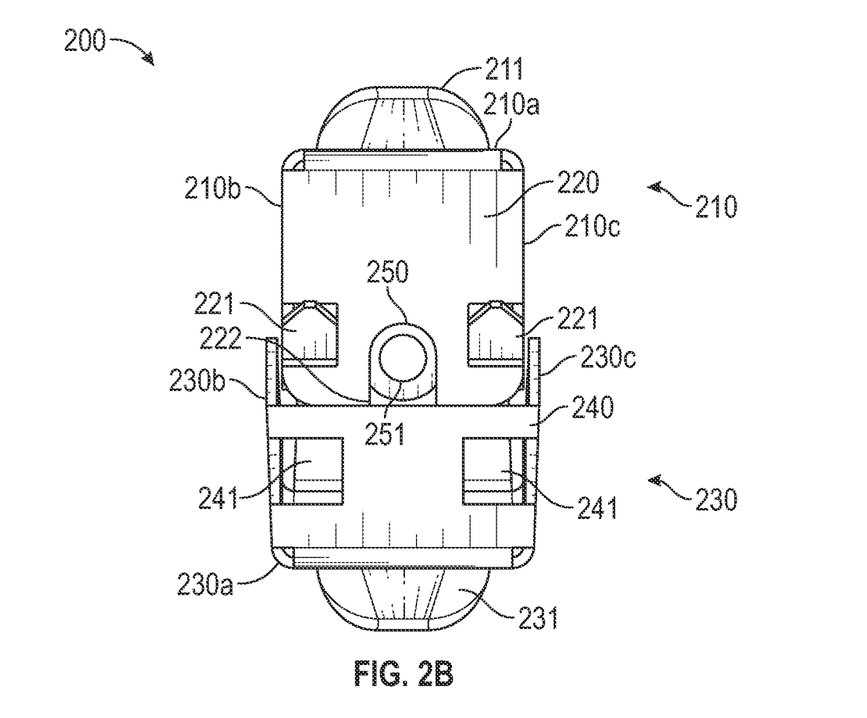
Figure 2C:
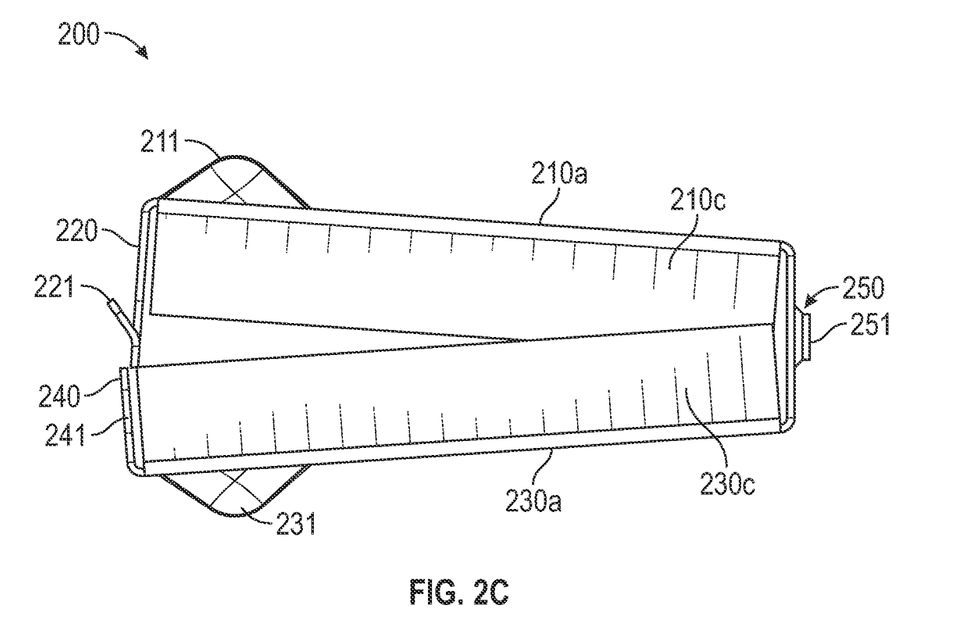
Figure 3:
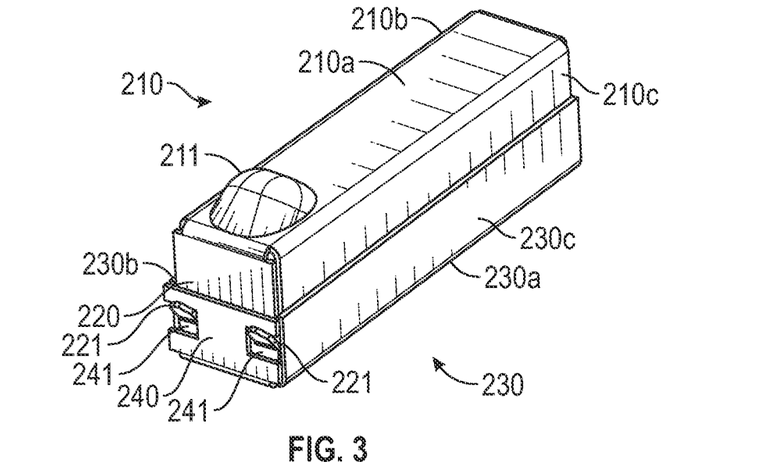
FIG. 3 is a top perspective view of the shield of FIGS. 2A-2C when in a locked position, in accordance with some embodiments, in accordance with some embodiments.
Figure 4:
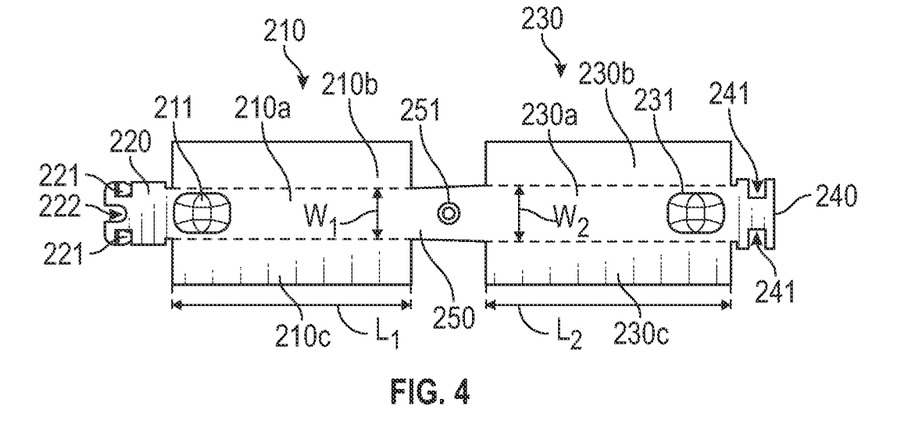
FIG. 4 is a pre-assembled view of the shield of FIGS. 2A-2C, in accordance with some embodiments.

FIGS. 2A-2C are top perspective, distal and side views respectively illustrating shield 200 in isolation when shield 200 is in an unlocked position. This unlocked position may represent the state of shield 200 before distal tip 122a has been withdrawn into shield 200. In contrast, FIG. 3 is a top perspective view illustrating shield 200 in a locked position. This locked position may represent the state of shield 200 after distal tip 122a has been withdrawn into shield 200 and shield 200 is being or has been separated from catheter adapter 111. FIG. 4 illustrates shield 200 in a pre-assembled state and represents that shield 200 may be manufactured from a single piece of flat material (e.g., sheet metal) and then folded into the unlocked position shown in FIGS. 2A-2C.

As shown in FIGS. 2A-4, shield 200 may include a top portion 210 and a bottom portion 230 that are connected by a proximal portion 250. The terms "top" and "bottom" are used relative to the orientation of shield 200 in the figures and are intended only to distinguish between the two portions and should not be construed as requiring the top portion to be on top during use of a PIVC. In fact, in some embodiments, shield 200 may be positioned within catheter adapter 111 in either orientation as will become apparent below. In contrast, the term "proximal" in proximal portion 250 is intended to represent that proximal portion 250 will be oriented proximally (i.e., away from distal tip 122a) during use. Shield 200 may also include a top distal portion 220 that extends from top portion 210 opposite proximal portion 250 and a bottom distal portion 240 that extends from bottom portion 230 opposite proximal portion 250. During use of shield 200, top distal portion 220 and bottom distal portion 240 will be oriented distally.

In some embodiments, top portion 210 may include a top surface 210a and side surfaces 210b, 210c that may be opposing and extend downwardly from top surface 210a. In some embodiments, and with reference to FIG. 4, top portion 210 may be formed by folding opposing side surfaces 210b, 210c downwardly relative to top surface 210a. Similarly, in some embodiments, bottom portion 230 may include a bottom surface 230a and opposing side surfaces 230b, 230c that may extend upwardly from bottom surface 230a. In some embodiments, and with reference to FIG. 4, bottom portion 230 may be formed by folding opposing side surfaces 230b, 230c upwardly relative to bottom surface 230a.

In some embodiments, the width ($W_1$) of top surface 210a may differ from the width ($W_2$) of bottom surface 230a. For example, $W_1$ may be less than $W_2$ so that side surfaces 210b, 210c may be positioned inside side surfaces 230b, 230c when shield 200 is assembled. Alternatively, $W_2$ may be less than $W_1$ so that side surfaces 230b, 230c may be positioned inside side surfaces 210b, 210c when shield 200 is assembled. In some embodiments, such as is represented in FIG. 4, a width of proximal portion 250 may be tapered to match the respective widths of top surface 210a and bottom surface 230a. In some embodiments, a length ($L_1$) of top portion 210 may differ from a length ($L_2$) of bottom portion 230. For example, $L_1$ may be less than $L_2$ so that top distal portion 220 may be positioned inside bottom distal portion 240 when shield 200 is assembled. Alternatively, $L_2$ may be less than $L_1$ so that bottom distal portion 240 may be positioned inside top distal portion 220 when shield 200 is assembled. In some embodiments, the widths of side surfaces 210b, 210c, 230b, and 230c relative to proximal portion 250 may be configured to cause side surfaces 210b, 210c to overlap side surfaces 230b, 230c when shield 200 is in the locked position as represented in FIG. 3. By overlapping, these side surfaces may prevent distal tip 122a from passing between the side surfaces once distal tip 122a is withdrawn into shield 200.

In some embodiments, a protrusion 211 may be formed on top surface 210a and a protrusion 231 may be formed on bottom surface 230a. In some embodiments, protrusions 211 and 231 may be aligned such that protrusion 211 may be positioned vertically above (or below) protrusion 231 when shield 200 is in a horizontal orientation. In such embodiments, opposing slots 115 in catheter adapter 111 may also be aligned to receive protrusions 211, 231 such as is shown in FIG. 5A. However, in other embodiments, protrusion 211 may be offset relative to protrusion 231, in which case, opposing slots 115 may be correspondingly offset.

In some embodiments, top distal portion 220 may include one or more tabs 221 that extend distally. In some embodiments, two tabs 221 may be formed on opposing sides of top distal portion 220. In some embodiments, each tab 221 may be formed by folding a portion of top distal portion 220 downwardly such that each tab 221 may extend distally and upwardly. In some embodiments, top distal portion 220 may include a distal needle opening 222 through which needle 122 may extend when shield 200 is in the unlocked position. In some embodiments, distal needle opening 222 may be positioned between tabs 221 with a clearance between the needle 122 and the distal needle opening 222. In some embodiments, the distal needle opening 222 may contact a surface of the needle 122, which may slide through the distal needle opening 222 and/or be pre-tensioned. In some embodiments, proximal portion 250 may include a proximal needle opening 251 that may also be sized to allow needle 122 but not bump 122b to pass therethrough. In some embodiments, the needle 122 may experience a low drag force in response to moving through the proximal needle opening 251.

In some embodiments, bottom distal portion 240 may include one or more notches 241 corresponding to the one or more tabs 221 of top distal portion 220. For example, in some embodiments, two notches 241 may be formed on opposing sides of bottom distal portion 240 and may be aligned with two tabs 221 formed on opposing sides of top distal portion 220. In some embodiments, each notch 241 may be positioned within bottom distal portion 240 such that a portion of bottom distal portion 240 remains positioned above the notch.

In some embodiments, distal needle opening 222 may be formed in bottom distal portion 240 rather than top distal portion 220. Similarly, in some embodiments, tabs 221 may be formed in bottom distal portion 240 while notches 241 may be formed in top distal portion 220. Accordingly, embodiments of shield 200 encompass multiple arrangements and orientations of distal needle opening 222, tab(s) 221 and notch(es) 241 on top distal portion 220 and bottom distal portion 240.

In some embodiments, when shield 200 is in the unlocked position, distal needle opening 222 may be positioned at least partially above bottom distal portion 240 so that needle 122 may pass through shield 200 via proximal needle opening 251 and distal needle opening 222. In this unlocked position, and while needle 122 remains within distal needle opening 222, needle 122 may contact top distal portion 220 and bottom distal portion 240 to prevent shield 200 from transitioning into the locked position. However, as distal tip 122a of needle 122 is withdrawn proximally into shield 200, top distal portion 220 and bottom distal portion 240 may be enabled to move towards one another to cause tabs 221 to insert into notches 241. In some embodiments, the interface between tabs 221 and notches 241 may retain shield 200 in the locked position. For example, because tabs 221 may be distally and upwardly oriented, when tabs 221 are contained in notches 241, tabs 221 may contact bottom distal portion 240 to prevent top portion 210 from pivoting away from bottom portion 230. In some embodiments, top distal portion 220 and bottom distal portion 240 may be configured to overlap sufficiently when shield 200 is in the locked position to cause distal needle opening 222 to be covered by bottom distal portion 240. In such embodiments, once shield 200 is in the locked position, even if distal tip 122a of needle 122 is positioned within distal needle opening 222, bottom distal portion 240 will prevent distal tip 122a from extending distally out from shield 200. In some embodiments, top distal portion 220 and bottom distal portion 240 may be at least as wide as top surface 210a and bottom surface 230a respectively and may abut side surfaces 210b, 210c and side surfaces 230b, 230c respectively to prevent distal tip 122a from passing therebetween.

In some embodiments, the above-described configuration of shield 200 may enable shield 200 to be manufactured by stamping a single piece of material. For example, a piece of sheet metal having the shape shown in FIG. 4 may be placed in a press where the sheet metal may be stamped to form protrusions 211, 231 and tabs 221. In such embodiments, once the sheet metal is stamped, it may be folded into the unlocked position.

Figure 5:
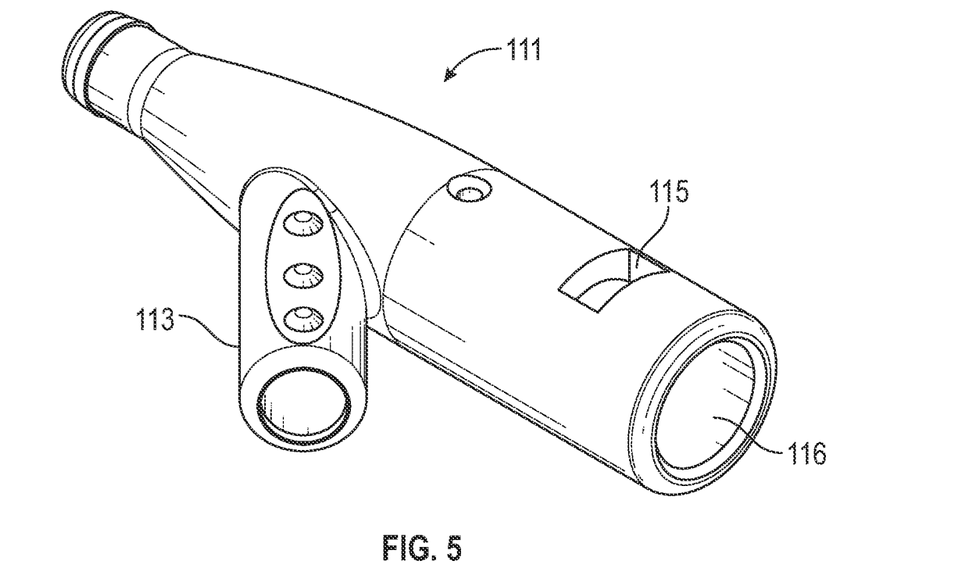
FIG. 5 is an isolated view of the catheter adapter of the PIVC of FIG. 1A, in accordance with some embodiments.
Figure 5A:
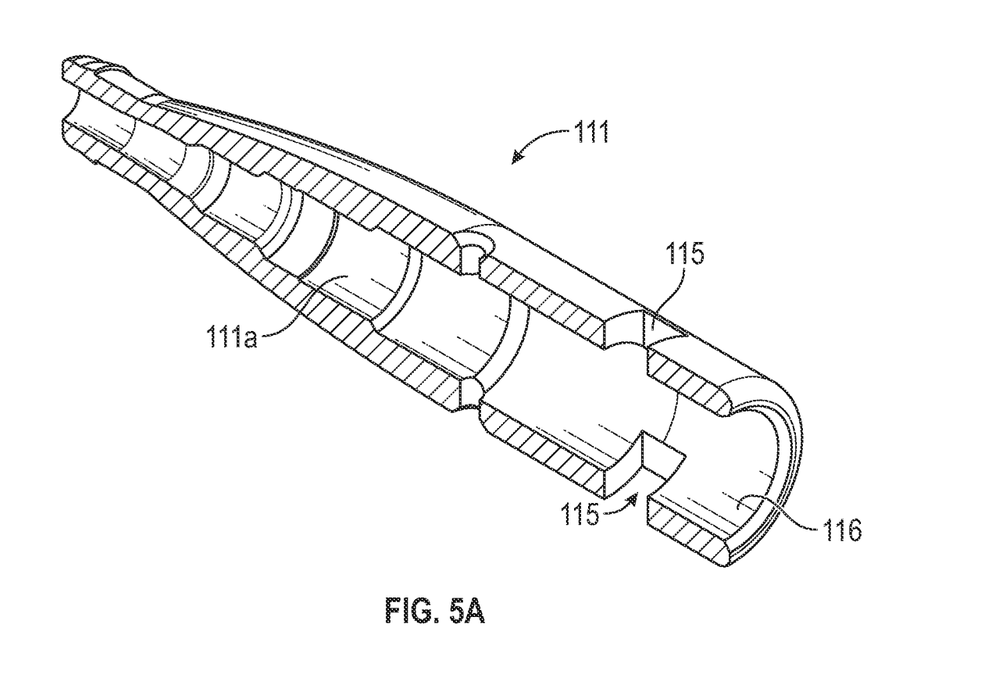
FIG. 5A is a cross-sectional view of the catheter adapter, in accordance with some embodiments.

FIG. 5 is a top (or bottom) perspective view and FIG. 5A is a corresponding cross-sectional view illustrating catheter adapter 111 in accordance with some embodiments. As shown, catheter adapter 111 may form a lumen 111a and may include slots 115 that may be positioned towards proximal end 116. As described above, slots 115 may be positioned within catheter adapter 111 to receive protrusions 211 and 231. In some embodiments, such as is shown in FIGS. 5 and 5A, slots 115 may extend fully through the sidewall of catheter adapter 111, whereas, in other embodiments, slots 115 may include internal indentations in the inner surface of the sidewall that do not extend through the outer surface of the sidewall.

Figure 6A:
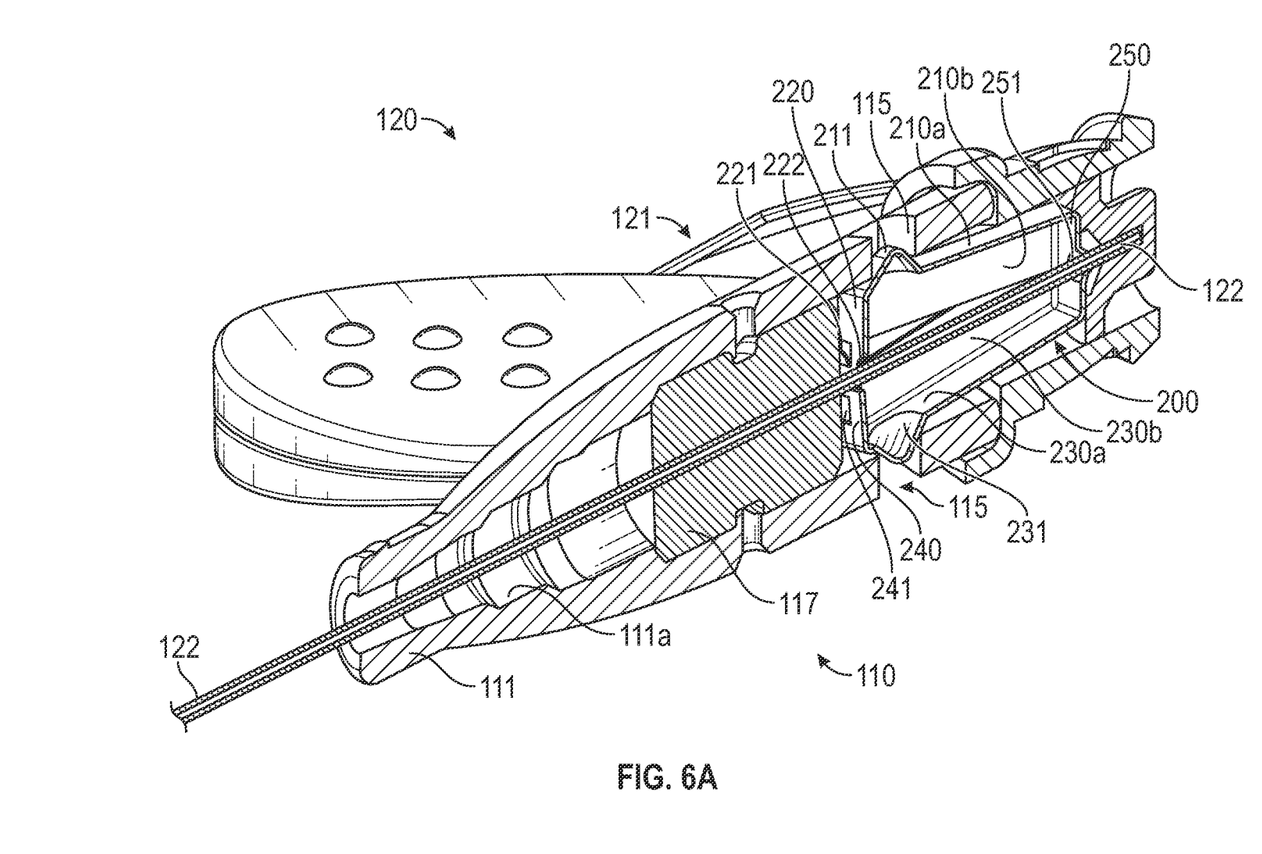
FIG. 6A is a cross-sectional view of the PIVC of FIG. 1A illustrating when the needle has not yet been withdrawn from the catheter, in accordance with some embodiments.
Figure 6B:
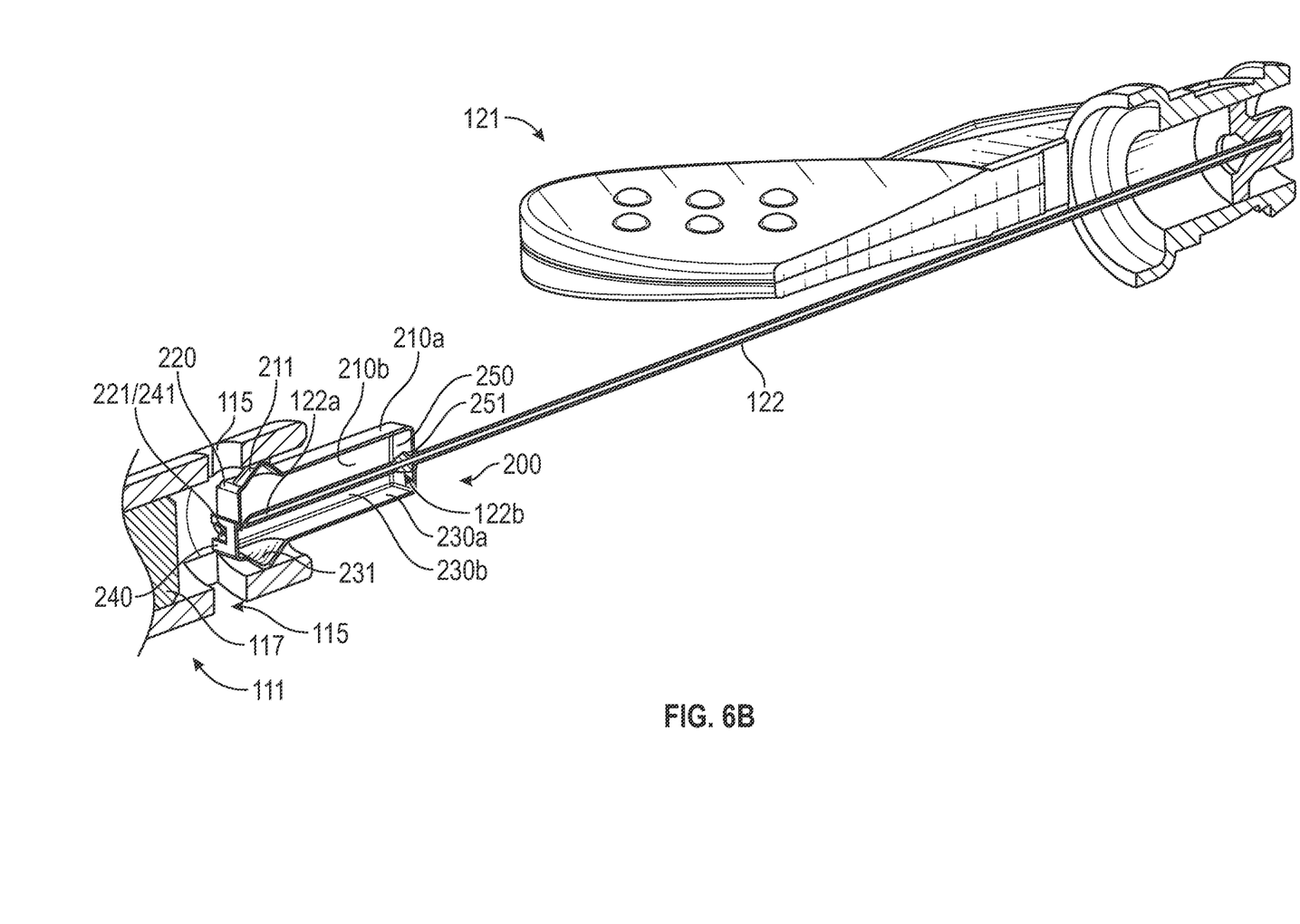
FIG. 6B is a cross-sectional view of the PIVC of FIG. 1A illustrating when the needle has been withdrawn to position the distal tip within the shield of FIGS. 2A-2C, in accordance with some embodiments.

FIGS. 6A and 6B are top (or bottom) cross-sectional perspective views illustrating PIVC 100. FIG. 6A represents PIVC 100 when needle assembly 120 has not been withdrawn from catheter assembly 110. In contrast, FIG. 6B represents PIVC 100 when needle assembly 120 is being withdrawn. In some embodiments, a septum 117 may be positioned within lumen 111a distal to slots 115 to thereby accommodate shield 200 within lumen 111a when needle assembly 120 is coupled to catheter assembly 110. In some embodiments, needle 122 may pass through septum 117. In some embodiments, the lumen 111a may not include the septum 117. In some embodiments, with needle assembly 120 coupled to catheter assembly 110, shield 200 may be positioned to cause protrusions 211 and 231 to be inserted into slots 115. In some embodiments, while needle 122 extends through proximal needle opening 251, top portion 210 and bottom portion 230 may be forced apart to cause protrusions 211, 231 to remain within slots 115. In other words, in some embodiments, proximal needle opening 251 may be configured so that the portion of needle 122 contained in proximal needle opening 251 retains top portion 210 and bottom portion 230 spaced sufficiently apart to prevent protrusions 211, 231 from escaping slots 115 while needle 122 remains in proximal needle opening 251.

In some embodiments, after catheter 112 has been inserted into the patient's vasculature, needle assembly 120 can be withdrawn proximally from catheter assembly 110. This proximal withdrawal of needle assembly 120 may cause distal tip 122a of needle 122 to pass proximally beyond top distal portion 220. With needle 122 no longer positioned in distal needle opening 222, top portion 210 and bottom portion 230 may be free to pivot towards one another. In some embodiments, the proximal movement of needle 122 may cause bump 122b to contact proximal portion 250 when distal tip 122a has passed into shield 200. Because bump 122b may have a larger cross-sectional area than proximal needle opening 251, continued proximal force on needle assembly 120 may cause shield 200 to be pulled proximally from catheter adapter 111. In some embodiments, as shield 200 is pulled proximally, protrusions 211, 231, which may form a ramped outer surface, may cause top portion 210 and bottom portion 230 to pivot inwardly towards one another. This inward pivoting may cause tabs 221 to insert into notches 241 to thereby lock shield 200 and may also cause protrusions 211, 231 to exit slots 115 thereby enabling shield 200 to be withdrawn from catheter adapter 111. The interface between tabs 221 and notches 241 may retain shield 200 in the locked position after shield 200 is separated from catheter adapter 111.

In some embodiments, top distal portion 220 and bottom distal portion 240 may be configured to not contact needle 122 while needle 122 extends into or through septum 117. For example, in FIG. 6A, bottom distal portion 240 is sized to be positioned below a center point of septum 117 through which needle 122 extends. As a result, needle 122 may be maintained above bottom distal portion 240 while needle 122 is positioned within septum 117. Similarly, distal needle opening 222 may be sized and positioned within top distal portion 220 so that no portion of top distal portion 220 contacts needle 122 until distal tip 122a has been withdrawn from septum 117. In this way, top distal portion 220 and bottom distal portion 240 may be prevented from imparting drag on needle 122 as needle 122 is withdrawn through septum 117.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:

1. A shield for a needle comprising:
   a top portion forming a top surface and opposing side surfaces that extend downwardly from the top surface;
   a bottom portion forming a bottom surface and opposing side surfaces that extend upwardly from the bottom surface;

a proximal portion that interconnects the top portion and the bottom portion, the proximal portion forming a proximal needle opening;
a top distal portion that extends downwardly from the top surface; and
a bottom distal portion that extends upwardly from the bottom surface;
wherein, when the shield is in an unlocked position, the top distal portion and the bottom distal portion are spaced to expose a distal needle opening, whereas, when the shield is in a locked position, the top distal portion and the bottom distal portion do not expose the distal needle opening,
wherein:
the top distal portion comprises one or more tabs and the bottom distal portion comprises one or more notches for receiving the one or more tabs to maintain the shield in the locked position, wherein the one or more notches face in a distal direction, wherein the one or more tabs are formed by folding a portion of the top distal portion downwardly such that the one or more tabs extend distally from the top distal portion and upwardly, wherein the one or more tabs of the top distal portion extend in the distal direction through the one or more notches when the shield is in the locked position.

2. The shield of claim 1, wherein the distal needle opening is formed in the top distal portion.

3. The shield of claim 2, wherein the one or more tabs comprise two tabs positioned on opposing sides of the top distal portion, the distal needle opening being formed between the two tabs.

4. The shield of claim 3, wherein the one or more notches comprise two notches positioned on opposing sides of the bottom distal portion.

5. The shield of claim 1, wherein, when the shield is in the unlocked position, the top distal portion and the bottom distal portion do not overlap, whereas, when the shield is in the locked position, the top distal portion and the bottom distal portion overlap.

6. The shield of claim 5, wherein, when the shield is in the unlocked position, the opposing side surfaces of the top portion partially overlap the opposing side surfaces of the bottom portion, whereas, when the shield is in the locked position, the opposing side surfaces of the top portion fully overlap the opposing side surfaces of the bottom portion.

7. The shield of claim 1, wherein the top surface and the bottom surface each form a protrusion for retaining the shield within a catheter adapter while the needle passes through the proximal needle opening and the distal needle opening.

8. The shield of claim 1, wherein the top portion, the bottom portion, the proximal portion, the top distal portion and the bottom distal portion are all formed from a single piece of material.

9. The shield of claim 8, wherein the single piece of material is a single piece of sheet metal.

10. An intravenous catheter system comprising:
a catheter assembly having a catheter adapter forming a lumen and a catheter that extends distally from the catheter adapter;
a needle assembly having a needle hub and a needle that extends distally from the needle hub, the needle assembly being configured to couple to the catheter assembly to cause the needle to extend through the lumen of the catheter adapter and the catheter; and
a shield positioned within the lumen of the catheter adapter, the shield comprising:
a top portion forming a top surface and opposing side surfaces that extend downwardly from the top surface;
a bottom portion forming a bottom surface and opposing side surfaces that extend upwardly from the bottom surface;
a proximal portion that interconnects the top portion and the bottom portion, the proximal portion forming a proximal needle opening;
a top distal portion that extends downwardly from the top surface; and
a bottom distal portion that extends upwardly from the bottom surface;
wherein, when the needle assembly is coupled to the catheter adapter, the needle extends through the proximal needle opening and a distal needle opening of the shield to thereby maintain the shield in an unlocked position, whereas, when the needle assembly is withdrawn proximally from the catheter assembly to cause a distal tip of the needle to pass through the distal needle opening, the shield transitions to a locked position in which the distal tip of the needle is prevented from passing distally through the distal needle opening,
wherein:
the top distal portion comprises one or more tabs and the bottom distal portion comprises one or more notches for receiving the one or more tabs to maintain the shield in the locked position, wherein the one or more notches face in a distal direction, wherein the one or more tabs are formed by folding a portion of the top distal portion downwardly such that the one or more tabs extend distally from the top distal portion and upwardly, wherein the one or more tabs of the top distal portion extend in the distal direction through the one or more notches when the shield is in the locked position.

11. The intravenous catheter system of claim 10, wherein the top surface and the bottom surface of the shield each form a protrusion, and wherein the catheter adapter comprises slots that receive the protrusions formed in the top and bottom surfaces when the shield is in the unlocked position.

12. The intravenous catheter system of claim 10, wherein the distal needle opening is formed in the top distal portion.

13. The intravenous catheter system of claim 10, wherein the one or more tabs comprise two tabs positioned on opposing sides of the top distal portion and the one or more notches comprise two notches positioned on opposing sides of the bottom distal portion.

14. The intravenous catheter system of claim 10, wherein the catheter assembly includes a septum positioned in the lumen of the catheter adapter distal to the shield, the needle extending through the septum when the needle assembly is coupled to the catheter assembly.

15. The intravenous catheter system of claim 10, wherein the top portion, the bottom portion, the proximal portion, the top distal portion and the bottom distal portion are all formed from a single piece of material.

16. A peripheral intravenous catheter comprising:
a catheter assembly having a catheter adapter forming a lumen and a catheter that extends distally from the catheter adapter;
a needle assembly having a needle hub and a needle that extends distally from the needle hub, the needle assembly being configured to couple to the catheter assembly to cause the needle to extend through the lumen of the catheter adapter and the catheter; and a shield positioned within the lumen of the catheter adapter, the shield being formed of a single piece of material and comprising:
- a top portion forming a top surface and opposing side surfaces that extend downwardly from the top surface;
- a bottom portion forming a bottom surface and opposing side surfaces that extend upwardly from the bottom surface;
- a proximal portion that interconnects the top portion and the bottom portion, the proximal portion forming a proximal needle opening;
- a top distal portion that extends downwardly from the top surface; and a bottom distal portion that extends upwardly from the bottom surface;

wherein, when the needle assembly is coupled to the catheter adapter, the needle extends through the proximal needle opening and a distal needle opening of the shield to thereby maintain the shield in an unlocked position, whereas, when the needle assembly is withdrawn proximally from the catheter assembly to cause a distal tip of the needle to pass through the distal needle opening, the shield transitions to a locked position in which the distal tip of the needle is prevented from passing distally through the distal needle opening, wherein:

the top distal portion comprises one or more tabs and the bottom distal portion comprises one or more notches for receiving the one or more tabs to maintain the shield in the locked position, wherein the one or more notches face in a distal direction, wherein the one or more tabs are formed by folding a portion of the top distal portion downwardly such that the one or more tabs extend distally from the top distal portion and upwardly, wherein the one or more tabs of the top distal portion extend in the distal direction through the one or more notches when the shield is in the locked position.

17. The peripheral intravenous catheter of claim 16, wherein the top surface and the bottom surface of the shield each form a protrusion, and wherein the catheter adapter comprises slots that receive the protrusions formed in the top and bottom surfaces when the shield is in the unlocked position.

* * * * *